United States Patent [19]

Junino et al.

[11] Patent Number: 4,845,293

[45] Date of Patent: Jul. 4, 1989

[54] DYEING COMPOSITION CONTAINING HALOGENATED 2-NITROANILINES

[75] Inventors: Alex Junino, Livry-Gargan; Gerard Lang, Saint-Gratien; Nicole Jehanno, Brunoy; Jean J. Vandenbosche, Aulnay-sous-Bois, all of France

[73] Assignee: L'Oreal, Paris, France

[21] Appl. No.: 15,033

[22] Filed: Feb. 17, 1987

[30] Foreign Application Priority Data

Feb. 14, 1986 [LU] Luxembourg .............................. 86309

[51] Int. Cl.$^4$ ...................... C07C 87/28; C07C 87/60; A61K 7/13
[52] U.S. Cl. ................................... 564/441; 564/367; 564/369; 564/371; 8/414; 8/415
[58] Field of Search ............... 564/367, 369, 371, 441; 8/414, 415

[56] References Cited

U.S. PATENT DOCUMENTS

| | | | |
|---|---|---|---|
| 1,105,447 | 7/1914 | Marx | 564/441 |
| 3,591,638 | 7/1971 | Halasz | 564/441 |
| 3,904,690 | 9/1975 | Kalopissis et al. | 564/441 |
| 3,973,900 | 8/1976 | Husemeyer et al. | 8/415 |
| 4,018,556 | 4/1977 | Kalopissis et al. | 8/415 |
| 4,419,101 | 12/1983 | Bugaut et al. | 564/441 |
| 4,637,821 | 1/1987 | Monnais et al. | 8/415 |
| 4,666,453 | 5/1987 | Junino et al. | 564/441 |
| 4,668,236 | 5/1987 | Grollier et al. | 8/415 |
| 4,704,474 | 11/1987 | Komrad et al. | 8/415 |

FOREIGN PATENT DOCUMENTS

| | | |
|---|---|---|
| 0132568 | 2/1985 | European Pat. Off. |
| 1506350 | 12/1967 | France |
| 1584965 | 1/1970 | France |
| 2090853 | 7/1982 | United Kingdom |

OTHER PUBLICATIONS

Tallec, A., *Chemical Abstracts*, vol. 65, No. 12127c, (1966).

White, W. N. et al., *Journal of Organic Chemsitry*, vol. 42, No. 1, pp. 166–169 (1977).

*Primary Examiner*—Glennon H. Hollrah
*Assistant Examiner*—Peter G. O'Sullivan
*Attorney, Agent, or Firm*—Cushman, Darby & Cushman

[57] ABSTRACT

A dyeing composition for keratinous fibres comprising a solvent and at least one dye which is a halogenated 2-nitro-aniline of formula:

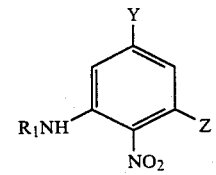

in which Y is a halogen and Z is a $NHR_2$ group or Y is hydrogen and Z is a halogen and $R_1$ and $R_2$, which may be identical or different, are each hydrogen, an alkyl group, a mono- or polyhydroxylated alkyl group, an alkyl group substituted with an alkoxy or hydroxyalkoxy group, or an aminoalkyl group, the amino group of which is optionally substituted with one or two alkyl or hydroxyalkyl groups, and it being possible for the nitrogen atom of the aminoalkyl group to form part of a heterocycle, all the abve alkyl groups or moieties containing from 1 to 6 carbon atoms, or, if the compound of formula (I) contains an amine group which can be salified, a cosmetically acceptable salt thereof.

27 Claims, No Drawings

DYEING COMPOSITION CONTAINING HALOGENATED 2-NITROANILINES

The present invention relates to a dyeing composition, containing halogenated nitroanilines, for keratinous fibers, and especially for human hair, to a dyeing method which employs the said dyeing composition and to new halogenated 2-nitroanilines and 2-nitrometaphenylene-diamines.

It is known that nitro derivatives of the benzene series may be used ot dye hair in a direct dyeing process or to provide additional sheens in an oxidation dyeing process.

The use of optionally halogenated 4-nitro-metaphenylenediamines in direct dyeing is known from French Pat. Nos. 1,508,405 and 1,584,965.

We have surprisingly discovered that it is possible to obtain hair dyeing compositions which have an improved light stability by using particular halogenated nitroanilines.

The present invention therefore provides a dyeing composition for keratinous fibers comprising a solvent and a tinctorially effective amount of at least one dye which is a halogenated 2-nitro-aniline of formula:

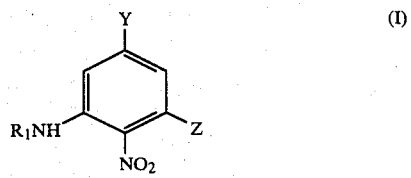

in which Y is a halogen and Z is a $NHR_2$ group or Y is hydrogen and Z is a halogen and $R_1$ and $R_2$, which may be identical or different, are each hydrogen, an alkyl group, a mono- or polyhydroxylated alkyl group, an alkyl group substituted with an alkoxy or hydroxyalkoxy group, or an aminoalkyl group, the amino group of which is optionally substituted with one or two alkyl or hydroxyalkyl groups, and it being possible for the nitrogen atom of the aminoalkyl group to form part of a heterocycle, all the above alkyl groups or moieties containing from 1 to 6 carbon atoms, or, if the compound of formula (I) contains an amino group which can be salified, a cosmetically acceptable salt thereof.

This composition is especially suitable for dyeing human hair.

The present invention also provides a halogenated 2-nitro-meta-phenylenediamine of formula:

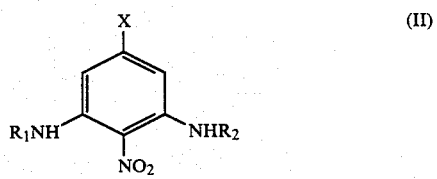

in which X is halogen and $R_1$ and $R_2$, which may be identical or different, are each hydrogen, an alkyl group, a mono- or polyhydroxylated alkyl group, an alkyl group substituted with an alkoxy or hydroxyalkoxy group, or an aminoalkyl group, the amino group of which is optionally substituted with one or two alkyl or hydroxyalkyl groups, it being possible for the nitrogen atom of the aminoalkyl group to form part of a heterocycle, all of the above alkyl groups or moieties containing from 1 to 6 carbon atoms and, if the compound of formula (II) contains an amine group which can be salified, a cosmetically acceptable salt thereof: with the proviso that $R_1$ and $R_2$ are not simultaneously hydrogen;

and a halogenated 2-nitroaniline of formula:

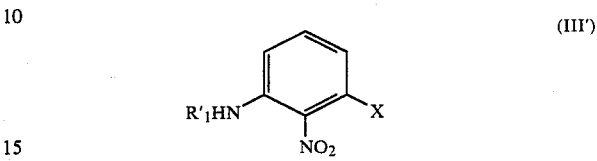

in which X is halogen and $R'_1$ is a polyhydroxylated alkyl group, an alkyl group substituted with an alkoxy or hydroxyalkoxy group or an aminoalkyl group, the amino group of which is optionally substituted with one or two alkyl or hydroxyalkyl groups, it being possible for the nitrogen atom of the aminoalkyl group to form part of a heterocycle, all of the above alkyl groups or moieties containing from 1 to 6 carbon atoms, and if the compound of formula (III') contains an amine group which can be salified, cosmetically acceptable salt thereof.

The compounds of formula (II) including those wherein $R_1$ and $R_2$ are simultaneously hydrogen have improved light stability as compared with the 4-nitro-metaphenylene-diamines of the French Patents mentioned above and have good stability during washing and adverse weather conditions.

The halogen atom may be chlorine, bromine or fluorine and preferably is chlorine.

The alkyl group or moiety preferably contains from 1 to 4 carbon atoms.

Preferred $R_1$ and $R_2$ groups are hydrogen and methyl, ethyl, n-propyl, n-butyl, β-hydroxyethyl, β-hydroxypropyl, γ-hydroxypropyl, β,γ-dihydroxypropyl, methoxyethyl, ethoxyethyl, β-hydroxyethoxyethyl, β-aminoethyl, β-hydroxyethylaminoethyl and β-diethylaminoethyl groups.

Preferred compounds of formula (I) used in the dyeing composition according to the present invention are 4-chloro-2,6-diaminonitrobenzene, 4-chloro-2-(β-hydroxyethyl)amino-6-(β-hydroxyethyl)aminonitrobenzene, 4-chloro-2-amino-6-methylaminonitrobenzene, 4-chloro-2-(β-aminoethyl)amino-6-(β-aminoethyl)aminonitrobenzene, 4-chloro-2-(β-hydroxyethoxyethyl)amino-6-(β-hydroxyethoxyethyl)aminonitrobenzene, 4-chloro-2-methylamino-6-methyl-aminonitrobenzene, 2-(β-hydroxyethyl)amino-6-chloronitrobenzene, 2-(β,γ-dihydroxypropyl)amino-6-chloronitrobenzene, 4-chloro-2-(β-hydroxypropyl)amino-6-(β-hydroxypropyl)-aminonitrobenzene, 4-chloro-2-(γ-hydroxypropyl)amino-6-(γ-hydroxypropyl)aminonitrobenzene, 4-chloro-2-(β-methoxyethyl)amino-6-(β-methoxyethyl)aminonitrobenzene, 4-chloro-2-[β-(β'-hydroxyethylamino)ethyl]amino-6-[β-(β'-hydroxyethylamino)ethyl]aminonitrobenzene, 4-chloro-2-(β-diethylaminoethyl)amino-6-(β-diethylaminoethyl)aminonitrobenzene and 4-chloro-2-(β,γ-dihydroxypropyl)amino-6-(β,γ-dihydroxypropyl)aminonitrobenzene.

Compounds of formulae (II) and (III') and, if they contain an amine group which can be salified, cosmetically acceptable salts thereof, can be used in the dyeing compositions of the present invention.

Preferred compounds of formula (II) of the present invention are: 4-chloro-2-(β-hydroxyethyl)amino-6-(β-hydroxyethyl)aminonitrobenzene, 4-chloro-2-amino-6-methylaminonitrobenzene, 4-chloro-(β-aminoethyl)amino-6-(β-aminoethyl)aminonitrobenzene, 4-chloro-2-(β-hydroxyethoxyethyl)amino-6-(β-hydroxyethoxyethyl)aminonitrobenzene, 4-chloro-2-methylamino-6-methylaminonitrobenzene, 4-chloro-2-(β-hydroxypropyl)amino-6-(β-hydroxypropyl)aminonitrobenzene, 4-chloro-2-(γ-hydroxypropyl)amino-6-(γ-hydroxypropyl)aminonitrobenzene, 4-chloro-2-(β-methoxyethyl)amino-6-(β-methoxyethyl)aminonitrobenzene, 4-chloro-2-[β-(β'-hydroxyethylamino)ethyl]amino-6-[β-(β'-hydroxyethylamino)ethyl]aminonitrobenzene, 4-chloro-2-(β-diethylaminoethyl)amino-6-(β-diethylaminoethyl)aminonitrobenzene and 4-chloro-2-(β,γ-dihydroxypropyl)amino-6-(β,γ-dihydroxypropyl)aminonitrobenzene.

Compounds of formula (II) may be prepared by reacting, in a first stage, ammonia or an amine of formula NH$_2$R$_1$, R$_1$ having the meaning defined above, with a 2,4,6-trihalogenonitrobenzene of formula (IV) wherein each X, which may be identical or different, is a halogen to obtain compound (V) which is then subjected, in a second stage, to the action of an amine of formula NH$_2$R$_2$, R$_2$ having the meaning defined above, or ammonia, to produce a compound of formula (II) according to the reaction scheme below:

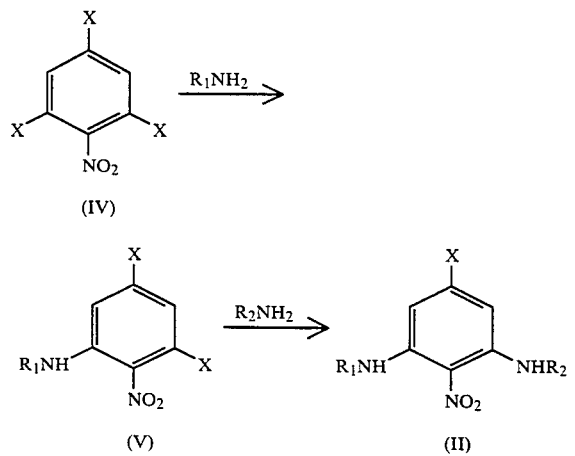

The compound of formula (II), in which the R$_2$ group is identical to the R$_1$ group, can be prepared in a single step starting with compound (IV). The synthesis of 2,6-diamino-4-chloronitrobenzene by the reaction of ammonia with 2,4,6-trichloronitrobenzene is known (Beil., vol. 13, p. 58).

The substitution of the halogens with amino groups NHR$_1$ and NHR$_2$ can be carried out in the absence of presence of a solvent. The solvents commonly used are lower alcohols or solvents such as dimethylformamide, dimethylsulphoxide, N-methylpyrrolidone or N,N'-dimethylpropylene urea. In the case where ammonia or the amine NH$_2$R$_1$ or NH$_2$R$_2$ is used in aqueous solution, it is preferable, for solubility reasons, to add a dissolving intermediary chosen from amongst those mentioned above.

By the term "lower" as used herein is meant groups containing from 1 to 6 carbon atoms, preferably from 1 to 4 carbon atoms.

The temperatures at which the reactions of substitution of the halo groups with the amino groups —NHR$_1$ and/or —NHR$_2$ are carried out may vary from 10° C. to the reflux temperature of ammonia, of the amine NH$_2$R$_1$ and/or NH$_2$R$_2$, of the solvent or of the reaction mixture. In general, the temperature is from 20° C. to 170° C.

In the case of gaseous ammonia or amines NH$_2$R$_1$ and/or NH$_2$R$_2$ with boiling temperatures lower than or equal to ambient temperature, the substitution may be carried out in an autoclave, a pressure of 25 kg/cm$^2$ generally being adequate.

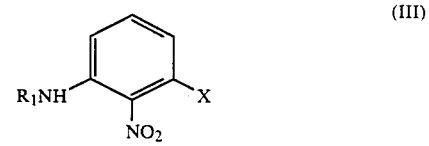

wherein X is a halogen, preferably chlorine, and R$_1$ is as defined above may be prepared from a 2,6-dihalonitrobenzene by the substitution of a halo group with a group NHR$_1$ according to the reaction scheme:

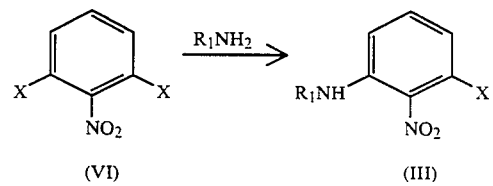

under similar conditions of substitution to those described in the case of the process for the preparation of compounds of formula (II).

When the halogen is chlorine, the substitution generally requires longer reaction periods and higher temperatures than in the case of compound (IV).

2,6-dihalonitrobenzenes can be prepared according to the processes described in the literature; for example, 2,6-dichlorobenzene may be prepared by the oxidation of 2,6-dichloroaniline either with trifluoroperacetic acid according to Organic Synthesis, vol. 49, page 47, or with a solution of sodium perborate in acetic acid according to Alexander McKillop and Jonathan A. Tarbin, Tetrahedron Letters, Vol. 24, no. 14, pages 1505–1508 (1983).

Comemrcial grade 2,4,6-trichloronitrobenzene used in the preparation of the compounds of formula (II) may also be prepared by this method.

A preferred compound of formula (III') of the present invention is 2-(β,γ-dihydroxy-propyl)amino-6-chloronitrobenzene.

The dyeing compositions according to the present invention may be used for the direct dyeing of keratinous fibers or for the oxidation dyeing of these fibers, in which case the compounds of formula (I) give additional sheens to the base color obtained by the oxidizing development of the oxidation dyestuff precursors.

The dyeing compositions according to the invention generally contain the compound of formula (I) or its salt in a proportion of from 0.001 to 5% by weight, preferably from 0.05 to 2% by weight, relative to the total weight of the composition.

The solvent is preferably water but organic solvents may also be added to the compositions in order to dissolve compounds which may not be sufficiently soluble in water. Examples of such solvents include lower alkanols such as ethanol and isopropanol, aromatic alcohols such as benzyl alcohol and phenoxyethanol, polyhydric alcohols such as glycerol, glycols or glycol ethers such as 2-butoxyethanol or 2-ethoxyethanol, ethylene glycol, propylene glycol and diethylene glycol monomethyl ether and monoethyl ether and mixtures thereof. These solvents are preferably present in a proportion of from 1 to 75% by weight, especially from 5 to 50% by weight, relative to the total weight of the composition.

These compositions may contain anionic, cationic, nonionic or amphoteric surfactants or their mixtures. These surfactants are generally present in a proportion of from 0.5 to 55% by weight, preferably from 4 to 40% by weight, relative to the total weight of the composition.

The compositions may be thickened, preferably with sodium alginate, gum arabic, xanthan gum, cellulose derivatives such as methyl cellulose, hydroxyethyl cellulose, hydroxypropylmethyl cellulose and carboxymethyl cellulose or various polymers which act as thickeners such as, more particularly, acrylic acid derivatives. It is also possible to use inorganic thickeners such as bentonite. These thickening agents are preferably present in a proportion of from 0.1 to 10% by weight, especially from 0.5 to 2% by weight, relative to the total weight of the composition.

The compositions may also contain various adjuvants commonly used in dyeing compositions for keratin fibers and hair, especially penetrants, dispersing agents, sequestering agents, film-forming agents, buffers and perfumes.

These compositions may be in diverse forms such as liquids, creams, gels or any other forms suitable for carrying out a hair of keratin fibers dyeing process. They may be packaged in the presence of a propellant in aerosol containers.

The pH of the dyeing compositions is generally from 3 to 11.5, preferably from 5 to 11.5. The pH may be adjusted to the desired value by using an alkalinizing agent such as ammonia, sodium, potassium or ammonium carbonate, sodium or potassium hydroxides, alkanolamines such as mono-, di- or triethanolamine, 2-amino-2-methylpropan-1-ol, 2-amino-2-methylpropane-1,3-diol and alkylamines such as ethylamine or triethylamine or by using an acidifying agent such as phosphoric, hydrochloric, tartaric, acetic, lactic or citric acid.

When the compositions are intended to be used in a direct dyeing process for the hair, they may additionally comprise at least one direct dyestuff other than that of formula (I) or a salt thereof such as an azo or anthraquinone dyestuff, for example, 1,4,5,8-tetraaminoanthraquinone, an indophenol, an inoaniline or a nitro dyestuff of the benzene series.

The concentrations of these direct dyestuffs other than the dyestuffs of formula (I) or a salt thereof is generally from 0.001 to 5% by weight relative to the total weight of the composition.

The present invention also provides a method for dyeing keratinous fibers, especially human hair, wherein a dyeing composition as defined above is applied to the fibers.

The present invention further provides a process for the direct dyeing of keratinous fibers wherein a composition as defined above is applied to the fibers for from 5 to 50 minutes, and the fibers are rinsed, washed with a shampoo if required, rinsed again and dried.

The compositions according to the present invention may also be employed in the form of hair setting lotions both for giving the hair a slight color or sheen and for improving the firmness of set. In this case, they may be in the form of aqueous, alcoholic or aqueous/alcoholic solutions containing at least one cosmetic resin.

The present invention also provides a method for dyeing keratinous fibers wherein a composition as defined above is applied to washed and rinsed fibers and, if required, the fibers are rolled and dried.

The cosmetic resins used in the setting lotions may especially by polyvinylpyrrolidone, crotonic acid/vinyl acetate, vinylpyrrolidone/vinyl acetate, maleic anhydride semi-esters/butylvinyl ether or maleic anhydride/methylvinyl ether copolymers, or maleic acid/methyl vinyl or butyl vinyl ether copolymers, as well as any other cationic, anionic, nonionic or amphoteric polymer commonly used in this type of composition. These cosmetic resins are generally used in the compositions of the invention in a proportion of from 0.1 to 4% by weight, preferably from 1 to 3% by weight, based on the total weight of the composition.

When the compositions according to the invention form oxidation dyeing compositions, meaning development with an oxidizing agent, the compounds of formula (I) or salts thereof according to the invention may be used essentially to provide a sheen in the final dyeing.

In this case, these compositions can contain precursors of oxidation dyestuffs and other direct dyestuffs if required.

They may contain, for example, para-phenylenediamines such as para-phenylenediamine, para-toluylenediamine, 2-chloro-para-phenylenediamine, 2,6-dimethylpara-phenylenediamine, 2,6-dimethyl-3-methoxy-para-phenylene-diamine, N-($\beta$-methoxyethyl)-para-phenylenediamine, N,N-($\beta$-hydroxyethyl)-para-phenylenediamine, N-ethyl-N-carbamyl-methyl-4-aminoaniline and their salts.

They may also contain para-aminophenols, for example para-aminophenol, N-methyl-para-aminophenol, 2-chloro-4-aminophenol, 3-chloro-4-aminophenol, 2-methyl-4-aminophenol and their salts; ortho-aminophenol or heterocyclic derivatives, for example 2,5-diaminopyridine and 7-aminobenzomorpholine.

The compositions according to the invention may contain, in combination with oxidation dyestuff precursors, couplers which are well known in the prior art.

Examples of couplers include meta-diphenols, metaaminophenols and their salts, metaphenylenediamines and their salts, meta-acylaminophenols, meta-ureidophenols and meta-carbalkoxyaminophenols. Other couplers may also be used such as $\alpha$-naphthol, couplers which contain an active methylene group such as diketone compounds and pyrazolones and heterocyclic couplers derived from pyridine and from benzomorpholine.

In addition to the oxidation dyestuff precursors, these compositions may contain reducing agents which are preferably present in a proportion of from 0.05 to 3% by weight relative to the total weight of the composition.

The oxidation dyestuff precursors are generally used, in the compositions of the invention, at a concentration of from 0.001 to 5% by weight, preferably from 0.03 to 2% by weight, based on the total weight of the composition. The couplers may also, for example, be present in a proportion of from 0.001 to 5% by weight, preferably from 0.015 to 2% by weight. The pH of the oxidation dyestuff compositions is preferably from 7 to 11.5 and may be adjusted using the alkalinizing agents defined above.

The present invention also provides a method for dyeing keratinous fibers, especially human hair, which employs development with an oxidizing agent wherein a composition as defined above is applied to the fibers. The color development may then be carried out slowly in the presence of oxygen in the air, but a chemical developer system, which is most frequently hydrogen peroxide, urea peroxide or a persalt, is preferably used. A 20 volume hydrogen peroxide solution is especially useful.

The composition with the oxidizing agent is preferably applied to the keratinous fibers for from 10 to 50 minutes, preferably 15 to 30 minutes, after which the keratinous fibers are rinsed, washed, for example with a shampoo, if required, rinsed again and dried.

The following Examples further illustrate the invention.

REFERENCE EXAMPLE

Preparation of 4-chloro-2,6-diminonitrobenzene

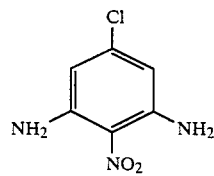

0.34 mole (76 g) of 2,4,6-trichloronitrobenzene is added to 400 ml of 28% ammonia in water and 100 ml of ethanol in an autoclave. The reaction medium is heated for 16 hours at 155°–160° C., the pressure being 20 kg/cm². The product expected precipitates on cooling. After draining and re-impasting in water until the water washings are neutral, it is dried under vacuum in the presence of phosphorous pentoxide. After recrystallizing from isopropanol in order to remove the resin, it melts at 202° C. (literature value 192°–194° C.).

Analysis of the product obtained gives the following results:

| Determination | Calculated for $C_6H_6ClN_3O_2$ | Observed |
|---|---|---|
| % C | 38.40 | 38.55 |
| % H | 3.20 | 3.26 |
| % N | 22.40 | 22.43 |
| % O | 17.06 | 16.88 |
| % Cl | 18.93 | 18.74 |

EXAMPLE 1

Preparation of 4-chloro-2-(β-hydroxyethyl)amino-6-(β-hydroxyethyl)aminonitrobenzene

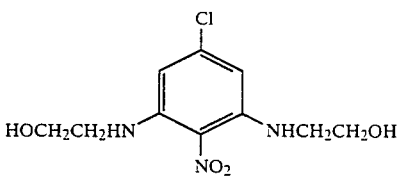

0.132 mole (30 g) of 2,4,6-trichloronitrobenzene is heated to 95° C. in 120 ml of ethanolamine. After 30 minutes, the reaction medium is poured into 240 g of an ice-water mixture. The product expected precipitates. It is drained, washed with water and then dried under vacuum in the presence of phosphorous pentoxide. After recrystallizing from absolute ethanol, it melts at 154° C.

Analysis of the product obtained gives the following results:

| Determination | Calculated for $C_{10}H_{14}ClN_3O_4$ | Observed |
|---|---|---|
| % C | 43.56 | 43.37 |
| % H | 5.08 | 5.11 |
| % N | 15.24 | 15.25 |
| % O | 23.23 | 23.45 |
| % Cl | 12.88 | 13.01 |

EXAMPLE 2

Preparation of 4-chloro-2-methylamino-6-methylaminonitrobenzene

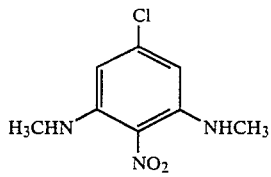

0.150 mole (34 g) of 2,4,6-trichloronitrobenzene is added in portions to 300 ml of a 30% solution of methylamine in absolute ethanol, at ambient temperature. After 23 hours of stirring at ambient temperature, the precipitate which essentially consists of chromatographically pure 4-chloro-2-methylamino-6-methylaminonitrobenzene which melts at 193° C. is filtered.

EXAMPLE 3

Preparation of 4-chloro-2-amino-6-methylaminonitrobenzene

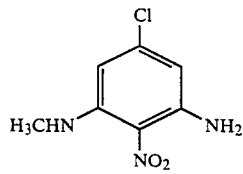

First stage

Preparation of 2,4-dichloro-6-methylaminonitrobenzene

The reaction is carried out in the same way as in Example 2. After filtering the precipitate consisting of 4-chloro-2-methylamino-6-methylaminonitrobenzene, the filtrate is collected and evaporated to dryness under reduced pressure. 800 ml of concentrated hydrochloric acid are added to the dry extract thereby obtained. The insoluble fraction is removed by draining. The product expected precipitates on diluting the filtrate with 650 ml of water. It is diluted with water and then dried under vacuum in the presence of phosphorous pentoxide. After recrystallizing from isopropanol and then from absolute ethanol, it melts at 120° C.

Analysis of the product obtained gives the following results:

| Determination | Calculated for $C_7H_6Cl_2N_2O_2$ | Observed |
|---|---|---|
| % C | 38.01 | 38.02 |
| % H | 2.71 | 2.72 |
| % N | 12.67 | 12.77 |
| % O | 14.48 | 14.40 |
| % Cl | 32.13 | 32.01 |

Second stage

Preparation of 4-chloro-2-amino-6-methylaminonitrobenzene 0.034 mole (7.5 g) of 2,4-dichloro-6-methylaminonitrobenzene is added to 100 ml of a 28% solution of ammonia in water and 50 ml of ethanol in an autoclave. The reaction medium is heated for 12 hours at 145°–150° C., the pressure being 12 kg/cm$^2$. The product expected precipitates from the reaction medium on cooling. After draining and re-impasting in water, it is dried by heating under vacuum in the presence of phosphorous pentoxide. Recrystallized from isopropanol, it melts at 129° C.

Analysis of the product obtained gives the following results:

| Determination | Calculated for $C_7H_8ClN_3O_2$ | Observed |
|---|---|---|
| % C | 41.69 | 41.71 |
| % H | 3.97 | 4.02 |
| % N | 20.84 | 20.80 |
| % O | 15.88 | 15.92 |
| % Cl | 17.62 | 17.49 |

EXAMPLE 4

Preparation of 4-chloro-2-(β-aminoethyl)amino-6-(β-aminoethyl)aminonitrobenzene

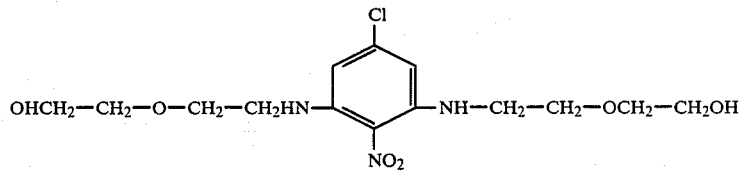

0.35 mole (79 g) of 2,4,6-trichloronitrobenzene is added to 280 ml of ethylenediamine diluted with 140 ml of dioxan, the temperature being maintained at 10° C. The mixture is heated for 2 hours at 50° C. The product expected precipitates on standing overnight at ambient temperature. After draining and re-impasting in water, the product is recrystallized from isopropanol in order to remove an insoluble product by filtering in the heated state. After drying under reduced pressure in the presence of phosphorous pentoxide, it melts at 113° C.

Analysis of the product obtained gives the following results:

| Determinaton | Calculated for $C_{10}H_{16}ClN_5O_2$ | Observed |
|---|---|---|
| % C | 43.87 | 43.76 |
| % H | 5.85 | 5.91 |
| % N | 25.59 | 25.49 |
| % O | 11.70 | 11.84 |
| % Cl | 12.98 | 12.82 |

EXAMPLE 5

Preparation of 4-chloro-2-(β-hydroxyethoxyethyl)amino6-(β-hydroxyethoxyethyl)aminonitrobenzene $$OHCH_2-CH_2-O-CH_2-CH_2HN-\underset{NO_2}{\underset{|}{\overset{\overset{Cl}{|}}{C_6H_2}}}-NH-CH_2-CH_2-OCH_2-CH_2OH$$

The mixture consisting of 0.1 mole (22.6 g) of 2,4,6-trichloronitrobenzene, 0.6 mole (63 g) of 2-(β-aminoethoxy)ethanol and 20 ml of dioxan is heated to reflux of the dioxon. After 4 hours, the reaction mixture is poured onto to 200 g of ice. The product expected crystallizes on acidifying with concentrated hydrochloric acid. After draining, washing with water and drying by heating under vacuum, the product is recrystallized from acetonitrile and then from toluene. It melts at 83° C.

Analysis of the product obtained gives the following results:

| Determinaton | Calculated for $C_{14}H_{22}N_3O_6Cl$ | Observed |
|---|---|---|
| % C | 46.22 | 45.93 |
| % H | 6.10 | 6.08 |
| % N | 11.55 | 11.79 |
| % O | 26.39 | 26.41 |

-continued

| Determination | Calculated for $C_{14}H_{22}N_3O_6Cl$ | Observed |
|---|---|---|
| % Cl | 9.74 | 9.81 |

EXAMPLE 6

Preparation of 2-(β-hydroxyethyl)amino-6-chloronitrobenzene (compound known by the formula III)

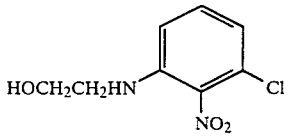

0.04 mole (7.7 g) of 2,6-dichloronitrobenzene in 30 ml of ethanolamine is heated for 8 hours at 70° C. The reaction mixture is poured onto ice, and then extracted with ethyl acetate. After washing and drying, the ethyl acetate phase is evaporated to dryness under vacuum. The dry extract is recrystallized from ethanol. The product obtained melts at 78° C. (literature value 78.5° C.).

EXAMPLE 7

Preparation of 2-(β,γ-dihydroxypropyl)amino-6-chloronitrobenzene

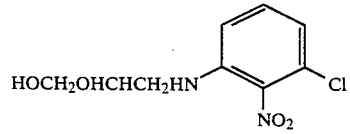

0.2 mole (38.4 g) of 2,6-dichloronitrobenzene and 0.6 mole (54.6 g) of 3-aminopropane-1,2-diol in 200 ml of 1-methyl-2-pyrrolidone are heated to 80° C. The reaction mixture is diluted with ice. The product expected precipitates. After recrystallizing from isopropanol, it melts at 126° C.

Analysis of the product obtained gives the following results:

| Determination | Calculated for $C_9H_{11}N_2O_4Cl$ | Observed |
|---|---|---|
| % C | 43.81 | 43.85 |
| % H | 4.46 | 4.45 |
| % N | 11.36 | 11.48 |
| % O | 25.96 | 25.84 |
| % Cl | 14.40 | 14.27 |

EXAMPLE 8

Preparation of 4-chloro-2-(β-hydroxypropyl)amino-6-(β-hydroxypropyl)aminonitrobenzene

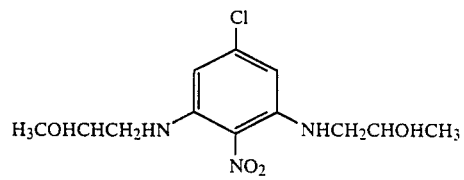

0.2 mole (45.3 g) of 2,4,6-trichloronitrobenzene is added in small portions to 180 ml of 3-amino-2-propanol heated to 80° C., with stirring. The reaction is exothermic. After heating for 3 hours 30 minutes, the reaction mixture is poured into 180 ml of ice-cold water. The product expected precipitates. It is drained, washed to neutrality with water and then dried under vacuum in the presence of phosphorous pentoxide. After recrystallization from 96° ethanol, it melts at 170° C.

Analysis of the product obtained gives the following results:

| Determination | Calculated for $C_{12}H_{18}N_3O_4Cl$ | Observed |
|---|---|---|
| % C | 47.45 | 47.40 |
| % H | 5.97 | 5.95 |
| % N | 13.83 | 13.62 |
| % O | 21.07 | 21.12 |
| % Cl | 11.67 | 11.84 |

EXAMPLE 9

Preparation of 4-chloro-2-(γ-hydroxypropyl)amino-6-(γ-hydroxypropyl)aminonitrobenzene

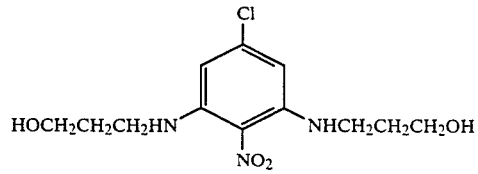

0.22 mole (50 g) of 2,4,6-trichloronitrobenzene is added in portions to 150 ml of 3-amino-1-propanol heated to 80° C., with stirring. Heating is continued for 1 hour 30 minutes after the addition is complete. The reaction medium is poured into 300 g of ice-cold water. An oil which crystallizes on adding concentrated hydrochloric acid is obtained. The precipitate of the expected product is drained, washed with a 2N solution of hydrochloric acid and then with water to neutrality. After drying at 40° C. in the presence of phosphorous pentoxide, it is recrystallized from 96° ethanol. It melts at 127° C.

Analysis of the product obtained gives the following results:

| Determination | Calculated for $C_{12}H_{18}N_3O_4Cl$ | Observed |
|---|---|---|
| % C | 47.45 | 47.41 |
| % H | 5.97 | 6.01 |

-continued

| Determination | Calculated for $C_{12}H_{18}N_3O_4Cl$ | Observed |
|---|---|---|
| % N | 13.83 | 13.99 |
| % O | 21.07 | 20.98 |
| % Cl | 11.67 | 11.89 |

EXAMPLE 10

Preparation of 4-chloro-2-($\beta$-methoxyethyl)amino-6-($\beta$-methoxyethyl)aminonitrobenzene

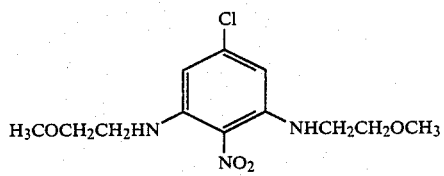

0.2 mole (45.3 g) of 2,4,6-trichloronitrobenzene is added in portions to 180 ml of 2-methoxyethylamine heated to 80° C., with stirring. Heating is continued for 2 hours 30 minutes after the addition is complete. The reaction medium is diluted with 180 ml of ice-cold water. The product expected precipitates. It is drained, washed with water and dried under vacuum at 60° C. in the presence of phosphorous pentoxide. Recrystallized from 96° ethanol, it melts at 90° C.

Analysis of the product obtained gives the following results:

| Determination | Calculated for $C_{12}H_{18}N_3O_4Cl$ | Observed |
|---|---|---|
| % C | 47.45 | 47.49 |
| % H | 5.97 | 6.01 |
| % N | 13.83 | 13.92 |
| % O | 21.07 | 20.91 |
| % Cl | 11.67 | 11.49 |

EXAMPLE 11

Preparation of 4-chloro-2-[$\beta$-($\beta'$-hydroxyethylamino)ethyl]amino-6-[$\beta$-($\beta'$-hydroxyethylamino)ethyl]aminonitrobenzene

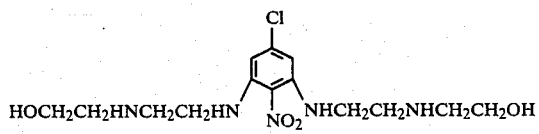

0.2 mole (45.3 g) of 2,4,6-trichloronitrobenzene is added in portions to 180 ml of 2-(2'-aminoethylamino)ethanol heated to 60° C., with stirring. The heating is continued for 1 hour after the addition is complete. The reaction medium is evaporated to dryness under reduced pressure. The dry extract is dissolved in 400 ml of absolute ethanol under reflux. The product expected crystallizes on cooling. Recrystallized from absolute ethanol, it melts at 130° C.

Analysis of the product obtained gives the following results:

| Determination | Calculated for $C_{14}H_{24}N_5O_4Cl$ | Observed |
|---|---|---|
| % C | 46.48 | 46.46 |
| % H | 6.68 | 6.67 |
| % N | 19.35 | 19.26 |
| % O | 17.69 | 17.65 |
| % Cl | 9.80 | 9.99 |

EXAMPLE 12

Preparation of 4-chloro-2-($\beta$-diethylaminoethyl)amino-6-($\beta$-diethylaminoethyl)aminonitrobenzene

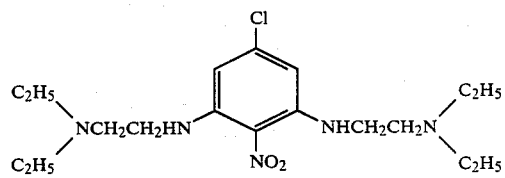

0.2 mole (45.3 g) of 2,4,6-trichloronitrobenzene is added in small portions to 180 ml of N,N-diethylethylenediamine heated to 60° C., with stirring. Heating is continued for 30 minutes after the addition is complete. The reaction medium is diluted with 180 ml of ice-cold water. The product expected precipitates. It is drained, washed with water and then dried under vacuum at 60° C. in the presence of phosphorous pentoxide. After recrystallizing from 96° ethanol, it melts at 90° C.

Analysis of the product obtained gives the following results:

| Determination | Calculated for $C_{18}H_{32}N_5O_2Cl$ | Observed |
|---|---|---|
| % C | 56.02 | 56.02 |
| % H | 8.36 | 8.30 |
| % N | 18.15 | 17.96 |
| % O | 8.29 | 8.46 |
| % Cl | 9.19 | 9.05 |

EXAMPLE 13

Preparation of 4-chloro-2-($\beta$,$\gamma$-dihydroxypropyl)amino-6-($\beta$,$\gamma$-dihydroxypropyl)aminonitrobenzene

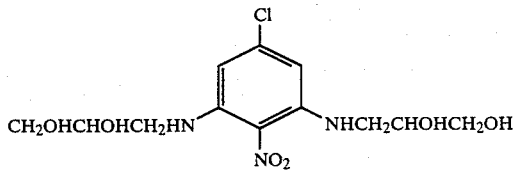

A mixture consisting of 0.1 mole (22.6 g) of 2,4,6-trichloronitrobenzene and 54.7 g of 3-aminopropane-1,2-diol in 20 ml of dioxan is heated under reflux. After heating for 4 hours, the dioxan is evaporated under reduced pressure. The oil obtained is diluted with approximately 300 ml of water. The product expected is obtained by chromatography under pressure in two operations. Approximately 200 ml of the aqueous solution of the product expected containing 3-aminopropane-1,2-diol are injected onto a $C_{18}RD$ chromatrography column (Waters Prep 500 apparatus). The product expected is eluted with a solution containing 35% methanol and 65% water. After evaporation of the fractions containing the product expected, a dry extract is obtained, which is recrystallized from 96° alcohol.

The product obtained melts at 146° C.

Elemental analysis of the product obtained gives the following results:

| Determination | Calculated for $C_{12}H_{18}N_3O_6Cl$ | Observed |
|---|---|---|
| % C | 42.92 | 42.87 |
| % H | 5.36 | 5.37 |
| % N | 12.52 | 12.39 |
| % O | 28.61 | 28.69 |
| % Cl | 10.58 | 10.47 |

EXAMPLE OF APPLICATION 1

The following dyeing mixture is prepared:

| | |
|---|---|
| 4-chloro-2,6-diaminonitrobenzene | 0.1 g |
| 2-butoxyethanol | 10 g |
| CELLOSIZE W.P. 03 - UNION CARBIDE (hydroxyethylcellulose) | 2 g |
| Cetyldimethylhydroxyethylammonium chloride | 2 g |
| 5% ammonia in water | 0.9 g |
| Water qs | 100 g |
| pH: 10 | |

This mixture, applied for 30 minutes at 30° C. to hair which is naturally 90% white, gives it, after shampooing and rinsing, an orange yellow color.

EXAMPLE OF APPLICATION 2

The following dyeing mixture is prepared:

| | |
|---|---|
| 4-chloro-2-($\beta$-hydroxyethyl)amino-6-($\beta$-hydroxyethyl)aminonitrobenzene | 0.1 g |
| 2-butoxyethanol | 10 g |
| CELLOSIZE W.P. 03 - UNION CARBIDE (hydroxyethylcellulose) | 2 g |
| Cetyldimethylhydroxyethylammonium chloride | 2 g |
| 5% ammonia in water | 0.9 g |
| Water qs | 100 g |
| pH: | 10 |

This mixture, applied for 30 minutes at 30° C. to bleached hair, gives it, after shampooing and rinsing, a light pink color with a golden sheen.

EXAMPLE OF APPLICATION 3

The following dyeing mixture is prepared:

| | |
|---|---|
| 4-chloro-2-($\beta$-aminoethyl)amino-6-($\beta$-aminoethyl)aminonitrobenzene | 0.4 g |
| Propylene glycol | 10 g |
| LAURAMIDE - WITCO (lauric acid monoethanolamide) | 1.5 g |
| Lauric acid | 1 g |
| CELLOSIZE W.P. 03 - UNION CARBIDE (hydroxyethylcellulose) | 5 g |
| Monoethanolamine | 2 g |
| Water qs | 100 g |
| pH: | 9.4 |

This mixture, applied for 20 minutes at 27° C. to bleached hair, gives it, after shampooing and rinsing, a bright orange color.

EXAMPLE OF APPLICATION 4

The following dyeing mixture is prepared:

| | |
|---|---|
| 4-chloro-2-amino-6-methylaminonitrobenzene | 0.15 g |
| 2-butoxyethanol | 10 g |
| COMPERLAN KD - HENKEL (coconut fatty acid diethanolamide) | 2.2 g |
| Lauric acid | 0.8 g |
| Ethylene glycol monoethyl ether | 2 g |
| 20% monoethanolamine solution in water | 1 g |
| Water qs | 100 g |
| pH: | 8.5 |

This mixture, applied for 25 minutes at 30° C. to hair which is naturally 90% white, gives it, after shampooing and rinsing, an orange-beige color.

EXAMPLE OF APPLICATION 5

The following dyeing mixture is prepared.

| | |
|---|---|
| 4-chloro-2($\beta$-hydroxyethoxyethyl)amino-6-($\beta$-hydroxyethoxyethyl)aminonitrobenzene | 0.5 g |
| 2-butoxyethanol | 10 g |
| CEMULSOL NP 4 - RHONE POULENC (nonylphenol with 4 moles of ethylene oxide) | 12 g |
| CEMULSOL NP 9 - RHONE POULENC (nonylphenol with 9 moles of ethylene oxide) | 15 g |
| Oleyl alcohol/glycerol polycondensate with 2 moles of glycerol | 1.5 g |
| Oleyl alcohol/glycerol polycondensate with 4 moles of glycerol | 1.5 g |
| 20% ammonia in water | 10 g |
| Water qs | 100 g |
| pH: | 11 |

This mixture, applied for 30 minutes at 27° C. to bleached hair, gives it, after shampooing and rinsing, an orange yellow color.

EXAMPLE OF APPLICATION 6

The following dyeing mixture is prepared:

| | |
|---|---|
| 4-chloro-2-($\beta$-aminoethyl)amino-6-($\beta$-aminoethyl)aminonitrobenzene | 0.14 g |
| 2-amino-3-nitrophenol | 0.05 g |
| 2-methyl-4-amino-5-nitro-N—$\beta$-aminoethyl-aniline hydrobromide monohydrate | 0.05 g |
| 3-nitro-4-N—$\beta$-aminoethyl-amino-N',N'—di-$\beta$-hydroxyethylaniline dihydrochloride | 0.14 g |
| Propylene glycol | 15 g |
| CELLOSIZE W.P. 03 - UNION CARBIDE (hydroxyethylcellulose) | 2 g |
| Cetyldimethylhydroxyethylammonium chloride | 2 g |
| Water qs | 100 g |
| pH: | 8.7 |

This mixture, applied for 20 minutes at 27° C. to permed hair, gives it, after shampooing and rinsing, a red copper color.

EXAMPLE OF APPLICATION 7

Oxidation dyeing

The following dyeing mixture is compared:

| | |
|---|---|
| 4-chloro-2,6-diaminonitrobenzene | 0.2 g |
| p-phenylenediamine | 0.15 g |
| Resorcin | 0.08 g |
| Meta-aminophenol | 0.06 g |
| 2,4-diaminophenoxyethanol dihydrochloride | 0.05 g |

-continued

| | |
|---|---|
| 4-(β-hydroxyethyl)amino-2-hydroxytoluene | 0.05 g |
| CARBOPOL 934 - GOODRICH CHEMICALS (polyacrylic acid crosslinked with a polyfunctional agent) | 3 g |
| 96° alcohol | 11 g |
| 2-butoxyethanol | 5 g |
| Cetyltrimethylammonium bromide | 2 g |
| TRILON B (ethylenediamine tetraacetic acid) | 0.2 g |
| 22° Be ammonia | 10 g |
| 35° Be sodium bisulphite | 1 g |
| Water qs | 100 g |
| pH: | 10 |

100 g of 20 volume hydrogen peroxide are added at the time of use. The mixture, applied for 30 minutes at 30° C. to hair which is bleached to a blonde color, gives it, after shampooing and rinsing, a dark, black chestnut-brown color.

EXAMPLE OF APPLICATION 8

Oxidation dyeing

The following dyeing mixture is prepared:

| | |
|---|---|
| 4-chloro-2-(β-aminoethyl)amino-6-(β-aminoethyl)aminonitrobenzene | 0.3 g |
| 2-(β-hydroxyethyl)amino-6-(β-hydroxyethyl)-aminonitrobenzene | 0.31 g |
| Para-phenylenediamine | 0.08 g |
| Resorcin | 0.09 g |
| 2-hydroxy-5-aminotoluene | 0.14 g |
| ALFOL C 16/18 - CONDEA (cetyl/stearyl alcohol) | 8 g |
| LANETTE E WAX - HENKEL (sodium cetyl stearyl sulphate) | 0.5 g |
| CEMULSOL B - RHONE POULENC (castor oil/ethylene oxide condensate) | 1 g |
| Oleic diethanolamide | 1.5 g |
| MASQUOL DTPA - PROTEX (diethylenetriamine-pentaacetic acid pentasodium salt) | 2.5 g |
| 22° Be ammonia | 11 g |
| Water qs | 100 g |
| pH: | 10.4 |

100 g of 20 volume hydrogen peroxide are added at the time of use. The mixture, applied for 30 minutes at 27° C. to hair which is naturally 90% white, gives it, after shampooing and rinsing, a violet chestnut-brown color.

EXAMPLE OF APPLICATION 9

The following dyeing mixture is prepared:

| | |
|---|---|
| 2-(β-hydroxyethyl)amino-6-chloronitrobenzene | 0.1 g |
| Ethyl alcohol | 10 g |
| CELLOSIZE W.P. 03 - UNION CARBIDE (hydroxyethylcellulose) | 2 g |
| Ammonium lauryl sulphate | 5 g |
| 1% by weight triethanolamine qs pH | 8 |
| Water qs | 100 g |

This mixture, applied for 35 minutes at 27° C. to permed grey hair, gives it, after shampooing and rinsing, a pale greenish yellow color.

EXAMPLE OF APPLICATION 10

The following dyeing mixture is prepared:

| | |
|---|---|
| 2-(β,γ-dihydroxypropyl)amino-6-chloro-nitrobenzene | 1 g |
| 96° ethanol | 10 g |
| ALFOL C 16/18 - CONDEA (cetyl stearyl alcohol) | 8 g |
| LANETTE E WAX - HENKEL (sodium cetyl/stearyl sulphate) | 0.5 g |
| CEMULSOL B - RHONE POULENC (castor oil/ethylene oxide condensate) | 1 g |
| Oleic diethanolamide | 1.5 g |
| 1% by weight triethanolamine qs pH | 7.5 |
| Water qs | 100 g |

This mixture, applied for 30 minutes at 27° C. to bleached hair, gives it, after shampooing and rinsing, a buttercup color.

EXAMPLE OF APPLICATION 11

The following dyeing mixture is prepared:

| | |
|---|---|
| 4-chloro-2-(γ-hydroxypropyl)amino-6-(γ-hydroxypropyl)aminonitrobenzene | 0.17 g |
| 2-butoxyethanol | 10 g |
| CELLOSIZE W.P. 03 - UNION CARBIDE (hydroxyethyl-cellulose) | 2 g |
| Ammonium lauryl sulphate | 5 g |
| 20% ammonia solution in water | 8 g |
| Water qs | 100 g |
| pH: | 10.6 |

This mixture, applied for 30 minutes at 35° C. to bleached hair, gives it, after shampooing and rinsing, a slightly grey red-orange color.

EXAMPLE OF APPLICATION 12

The following dyeing mixture is prepared:

| | |
|---|---|
| 4-chloro-2-(β-hydroxypropyl)amino-6-(β-hydroxypropyl)aminonitrobenzene | 0.223 g |
| 96° alcohol | 10 g |
| ALFOL C 16/18 - CONDEA (cetyl/stearyl alcohol) | 8 g |
| LANETTE E WAX - HENKEL (sodium cetyl/stearyl sulphate) | 0.5 g |
| CEMULSOL B - RHONE POULENC (castor oil/ethylene oxide condensate) | 1 g |
| Oleic diethanolamide | 1.5 g |
| 20% ammonia solution in water | 4 g |
| Water qs | 100 g |
| pH: | 10.1 |

This mixture, applied for 30 minutes at 35° C. to bleached hair, gives it, after shampooing and rinsing, a light yellowish brown color.

EXAMPLE OF APPLICATION 13

The following dyeing mixture is prepared:

| | |
|---|---|
| 4-chloro-2-(β,γ-dihydroxypropyl)amino-6-(β,γ-dihydroxypropyl)aminonitrobenzene | 0.155 g |
| 2-butoxyethanol | 10 g |
| CARBOPOL 934 - GOODRICH CHEMICALS (crosslinked polyacrylic acid) | 2 g |
| Triethanolamine | 3 g |
| Water qs | 100 g |
| pH: | 8.4 |

This mixture, applied for 30 minutes at 35° C. to bleached hair, gives it, after shampooing and rinsing, a slightly grey reddish orange color.

EXAMPLE OF APPLICATION 14

The following dyeing mixture is prepared:

| | |
|---|---|
| 4-chloro-2-(β-methoxyethyl)amino-6-(β-methoxyethyl)aminonitrobenzene | 0.11 g |
| 96° alcohol | 16 g |
| CELLOSIZE W.P. 03 - UNION CARBIDE | 2 g |
| Cetyldimethylhydroxyethylammonium chloride | 2 g |
| 20% ammonia solution in water | 4 g |
| Water qs | 100 g |
| pH: | 11 |

This mixture, applied for 25 minutes at 35° C. to permed hair, gives it, after shampooing and rinsing, a slightly grey yellowish brown color.

EXAMPLE OF APPLICATION 15

The following dyeing mixture is prepared:

| | |
|---|---|
| 4-chloro-2-[β-(β'-hydroxyethyl)aminoethyl]-amino-6-[β-(β'-hydroxyethyl)aminoethyl]amino-nitrobenzene | 0.134 g |
| 2-butoxyethanol | 11 g |
| CELLOSIZE W.P. 03 - UNION CARBIDE | 2 g |
| Ammonium lauryl sulphate | 5 g |
| Triethanolamine | 5 g |
| Water qs | 100 g |
| pH: | 9.2 |

This mixture, applied for 25 minutes at 35° C. to bleached hair, gives it, after shampooing and rinsing, a medium orange color.

EXAMPLE OF APPLICATION 16

The following dyeing mixture is prepared:

| | |
|---|---|
| 4-chloro-2-(β-diethylaminoethyl)amino-6-(β-diethylaminoethyl)aminonitrobenzene | 0.092 g |
| 2-butoxyethanol | 8 g |
| CELLOSIZE W.P. 03 - UNION CARBIDE | 2 g |
| Cetyldimethylhydroxyethylammonium chloride | 2 g |
| 20% ammonia solution in water | 2.5 g |
| Water qs | 100 g |
| pH: | 10.9 |

This mixture, applied for 25 minutes at 35° C. to permed hair, gives it, after shampooing and rinsing, a light olive brown color.

We claim:

1. A dyeing composition for keratinous fibers comprising a solvent selected from the group consisting of water, a lower alcohol, an aromatic alcohol, a polyhydric alcohol, a glycol, a glycol ether and a mixture thereof and a tinctorially effective amount of at least one dye which is a halogenated 2-nitro-aniline of the formula:

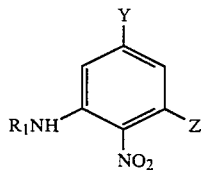

in which Y is a halogen and Z is a NHR₂ group of Y is hydrogen and Z is a halogen and R₁ and R₂, which may be identical or different, are each hydrogen, an alkyl group, a mono- or polyhydroxylated alkyl group, an alkyl group substituted with an alkoxy or hydroxyalkoxy group, or an aminoalkyl group, the amino group of which is optionally substituted with one or two alkyl or hydroxyalkyl groups, all the above alkyl groups or moieties containing from 1 to 6 carbon atoms, or, if the compound of formula (I) contains an amine group which can be salified, a cosmetically acceptable salt thereof.

2. A dyeing composition for keratinous fibers comprising a solvent selected from the group consisting of water, a lower alcohol, an aromatic alcohol, a polyhydric alcohol, a glycol, a glycol ether and a mixture thereof and a tinctorially effective amount of at least one dye having the formula

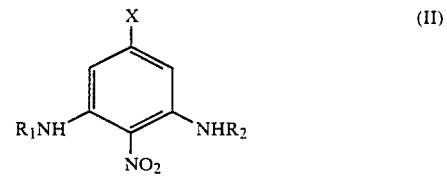

wherein
X is halogen and
R₁ and R₂ which may be identical or different, are each hydrogen, an alkyl group, a mono- or polyhydroxylated alkyl group, an alkyl group substituted with an alkoxy or hydroxyalkoxy group, or an aminoalkyl group, the amino group of which is optionally substituted with one or two alkyl or hydroxyalkyl groups, all the above alkyl groups or moieties containing from 1 to 6 carbon atoms, or, if the compound of formula (II) contains an amine group which can be salified, a cosmetically acceptable salt thereof.

3. A dyeing composition according to claim 1 wherein the halogenated 2-nitroaniline has the formula:

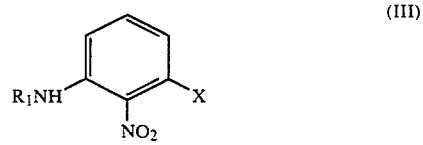

in which X is a halogen and R₁ is as defined in claim 1.

4. A dyeing composition according to claim 1 wherein the halogen is chlorine and R₁ and R₂, which may be identical or different, are each hydrogen or a methyl, ethyl, n-propyl, n-butyl, β-hydroxyethyl, β-hydroxypropyl, γ-hydroxypropyl, β,γ-dihydroxypropyl, methoxyethyl, ethoxyethyl, β-hydroxyethoxyethyl, β-aminoethyl, β-hydroxyethylaminoethyl or β-diethylaminoethyl group.

5. A dyeing composition according to claim 1 wherein the halogenated 2-nitroaniline is selected from the group consisting of: 4-chloro-2,6-diaminonitrobenzene, 4-chloro-2-(β-hydroxyethyl)amino-6-(β-hydroxyethyl)aminonitrobenzene, 4-chloro-2-amino-6-methylaminonitrobenzene, 4-chloro-2-(β-aminoethyl)amino-6-(β-aminoethyl)amino-nitrobenzene, 4-chloro-2-(β-hydroxyethoxyethyl)amino-6-(β-hydroxyethyoxyethyl)aminonitrobenzene, 2-(β-hydroxyethyl)amino-6-chloronitrobenzene, 2-(β,γ-dihydroxypropyl)amino-6-chloronitrobenzene, 4-chloro-2-methyl-amino-6-methylaminonitrobenzene, 4-chloro-2-(β-hydroxypropyl)amino-6-(β-hydroxypropyl)aminonitrobenzene, 4-chloro-2-(γ-hydroxypropyl)amino-6-(γ-hydroxypropyl)aminonitrobenzene, 4-chloro-2-(β-methoxyethyl)amino-6-(β-methoxyethyl)amino-nitrobenzene, 4-chloro-2-[β-(B'-hydroxyethylamino)ethyl]-amino-6-[β-(β'-hydroxyethylamino)ethyl]aminonitrobenzene, 4-chloro-2-(β-diethylaminoethyl)amino-6-(β-diethylaminoethyl)aminonitrobenzene and 4-chloro-2-(β,γ-dihydroxypropyl)amino-6-(β,γ-dihydroxypropyl)aminonitrobenzene.

6. A dyeing composition according to claim 1 which comprises from 0.001 to 5% by weight, relative to the total weight of the composition, of the dye.

7. A dyeing composition according to claim 6 which comprises from 0.05 to 2% by weight of the dye.

8. A dyeing composition according to claim 1 which has a pH of from 3 to 11.5.

9. A dyeing composition according to claim 8 which has a pH of from 5 to 11.5.

10. A dyeing composition according to claim 1 which additionally comprises an anionic, cationic, nonionic or amphoteric surfactant or a mixture thereof, a thickener, a dispersant, a penetrant, a sequestrant, a film-forming agent, a buffer, a perfume or an alkalinizing or acidifying agent.

11. A Dyeing composition according to claim 1 which is suitable for dyeing human hair.

12. A dyeing composition according to claim 1 suitable for use in the direct dyeing of human hair which additioally comprises at least one direct dyestuff other than one as defined in claim 1 which is an azo dyestuff, an anthraquinone dyestuff, an indophenol, an indoaniline or a nitro derivative of the benzene series.

13. A dyeing composition according to claim 1 suitable for use as a hair setting lotion, which is in the form of an aqueous, alcoholic or aqueous/alcoholic solution and which contains at least one cosmetic resin.

14. A dyeing composition according to claim 1 suitable for the oxidation dyeing of hair which additionally comprises at least one oxidation dyestuff precursor and, if required, at least one coupler.

15. A method of dyeing keratinous fibers wherein a dyeing composition as defined in claim 1 is applied to the fibers.

16. A method according to claim 15 wherein the keratinous fibers are human hair.

17. A method for the direct dyeing of keratinous fibers wherein a dyeing composition as defined in claim 12 is applied to the fibers for from 5 to 50 minutes, and the fibers are rinsed, washed, if required with a shampoo, rinsed again and dried.

18. A method according to claim 17 wherein the keratinous fibers are human hair.

19. A method for dyeing keratinous fibers wherein a composition as defined in claim 13 is applied to washed and rinsed fibers and, if required, the fibers are rolled and dried.

20. A method according to claim 19 wherein the keratinous fibers are human hair.

21. A method for dyeing keratinous fibers which employs development with an oxidizing agent wherein a composition as defined in claim 14 mixed with an oxidizing agent or dyestuff precursor is applied to the fibers for from 10 to 50 minutes, and the fibers are rinsed, washed if required, rinsed again and dried.

22. A method according to claim 21 wherein the keratinous fibers are human hair.

23. A halogenated 2-nitro-meta-phenylenediamine of formula:

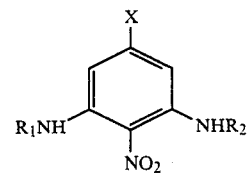

(II)

in which X is halogen and $R_1$ and $R_2$, which may be identical or different, are each hydrogen, an alkyl group, a mono- or polyhydroxylated alkyl group, and alkyl group substituted with an alkoxy or hydroxyalkoxy group, or an aminoalkyl group, the amino group of which is optionally substituted with one or two alkyl or hydroxyalkyl groups, all of the above alkyl groups or moieties containing from 1 to 6 carbon atoms and, if, the compound of formula (II) contains an amine group which can be salified, a cosmetically acceptable salt thereof; with the proviso that $R_1$ and $R_2$ are not simultaneously hydrogen.

24. A compound according to claim 23 wherein X is chlorine and $R_1$ and $R_2$, which may be identical or different, are each hydrogen or a methyl, ethyl, n-propyl, n-butyl, β-hydroxyethyl, β-hydroxypropyl, γ-hydroxypropyl, β,γ-dihydroxypropyl, methoxyethyl, ethoxyethyl, β-hydroxyethoxyethyl, β-aminoethyl, β-hydroxyethylaminoethyl or β-diethylaminoethyl group.

25. The compound of claim 23 selected from the group consisting of 4-chloro-2-(β-hydroxyethyl)amino-6-(β-hydroxyethyl)aminonitrobenzene, 4-chloro-2-amino-6-methylaminonitrobenzene, 4-chloro-(β-aminoethyl)amino-6-(β-aminoethyl)aminonitrobenzene, 4-chloro-2-(β-hydroxyethoxyethyl)amino-6-(β-hydroxyethoxyethyl)aminonitrobenzene, 4-chloro-2-methylamino-6-methyl-aminonitrobenzene, 4-chloro-2-(β-hydroxypropyl)amino-6-(β-hydroxypropyl)-aminonitrobenzene, 4-chloro-2-(γ-hydroxypropyl)amino-6-(γ-hydroxypropyl)aminonitrobenzene, 4-chloro-2-(β-methoxyethyl)-amino-6-(β-methoxyethyl)amino-nitrobenzene, 4-chloro-2-[β-(β'-hydroxyethylamino)ethyl]-amino-6-[β-(β'-hydroxyethylamino)ethyl]aminonitrobenzene, 4-chloro-2-(β-diethylaminoethyl)amino-6-(β-diethylaminoethyl)aminonitrobenzene and 4-chloro-2-(β,γ-dihydroxypropyl)amino-6-(β,γ-dihydroxypropyl)aminonitrobenzene.

26. A halogenated 2-nitroaniline of formula:

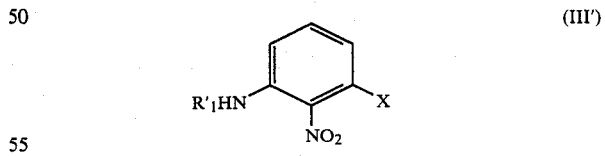

(III')

in which X is a halogen and $R'_1$ is a polyhydroxylated alkyl group, an alkyl group substituted with an alkoxy or hydroxyalkoxy group or an aminoalkyl group, the amino group of which is optionally substituted with one or two alkyl or hydroxyalkyl groups, all of the above alkyl groups or moieties containing from 1 to 6 carbon atoms, and if the compound of formula (III') contains an amine group which can be salified, a cosmetically acceptable salt thereof.

27. The compound of claim 26 which is 2-(β,γ-dihydroxypropyl)amino-6-chloro-nitrobenzene.

* * * * *